United States Patent [19]

Dorlars

[11] 4,347,357
[45] Aug. 31, 1982

[54] PROCESS FOR THE PREPARATION OF V-TRIAZOLE COMPOUNDS

[75] Inventor: Alfons Dorlars, Leverkusen, Fed. Rep. of Germany

[73] Assignee: Bayer Aktiengesellschaft, Leverkusen, Fed. Rep. of Germany

[21] Appl. No.: 259,307

[22] Filed: Apr. 30, 1981

[30] Foreign Application Priority Data

May 22, 1980 [DE] Fed. Rep. of Germany ....... 3019521

[51] Int. Cl.$^3$ ............................................. C07D 55/02
[52] U.S. Cl. ..................................... 542/462; 548/255
[58] Field of Search .......................... 542/462; 548/255

[56] References Cited

U.S. PATENT DOCUMENTS

| | | | |
|---|---|---|---|
| 3,666,758 | 5/1972 | Dorlars | 548/255 |
| 3,947,412 | 3/1976 | Claussen et al. | 548/255 |
| 3,965,094 | 6/1976 | Claussen et al. | 548/255 |
| 4,017,509 | 4/1977 | Tsujimoto et al. | 548/255 |
| 4,167,626 | 9/1979 | Fleck et al. | 548/255 |
| 4,217,449 | 8/1980 | Dorlars et al. | 548/255 |
| 4,233,440 | 11/1980 | Dorlars | 542/42 C |

OTHER PUBLICATIONS

Lind et al., Chem. Abstracts 80, (1974), #108449.

*Primary Examiner*—Arthur P. Demers
*Attorney, Agent, or Firm*—Sprung, Horn, Kramer & Wooods

[57] ABSTRACT

Water-soluble 2-aryl-v-triazoles are obtained in a simple manner and in surprisingly good yields when corresponding α-oximinoarylhydrazones are heated to temperatures of 120°–200° C. in water or predominantly aqueous media in the absence of the cyclizing agents which are otherwise customary.

The process products are valuable UV-absorbers or optical brighteners.

2 Claims, No Drawings

PROCESS FOR THE PREPARATION OF V-TRIAZOLE COMPOUNDS

The invention is an improved process for the preparation of water-soluble 2-aryl-v-triazole compounds by cyclodehydration of corresponding α-oximinoarylhydrazones.

2-Aryl-v-triazoles, which, inter alia, are industrially valuable UV absorbers and optical brighteners, have hitherto been prepared exclusively by the action of acylating agents, such as acid anhydrides, acid halides, urea and isocyanates, on suitable oximinohydrazones (compare German Offenlegungsschrift 2,338,881, German Auslegeschrift 2,746,000, U.S. Patent Nos. 3,666,758, 3,947,412, 3,965,094 and British Patent Specification 1,405,218).

These processes, which have in many cases proved to be useful per se, nevertheless have the disadvantage that the cyclising agent, which incidentally is relatively expensive, severely pollutes the effluent.

It has now been found that water-soluble 2-aryl-v-triazoles are obtained in a simple manner and in surprisingly good yields when the α-oximinoarylhydrazones are heated to temperatures of 120°–200° C. in water or predominantly aqueous media in the absence of the cyclising agents which are otherwise customary.

The new process is particularly suitable for the preparation of triazoles which correspond to the formula

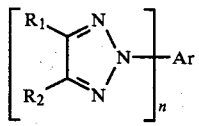

(I)

wherein
R$_1$ and R$_2$ independently of one another denote optionally substituted alkyl or aryl,
Ar denotes aryl and
n denotes the number 1 or 2,
and in which at least one of the aryl radicals, preferably the radical Ar, contains at least one substituent conferring solubility in water.

Suitable alkyl radicals are those with 1–4 C atoms.

Suitable aryl radicals R$_1$, R$_2$ and Ar are phenyl radicals, which can be substituted by customary, non-chromophoric substituents, such as halogen, C$_{1-4}$-alkyl, C$_{1-4}$-alkoxy or phenyl.

The radical Ar can furthermore belong to the naphthalene, diphenylmethane, diphenylethane, stilbene or tolane series. These radicals can also be substituted in the customary manner.

By "halogen" there is understood F, Br and, in particular, Cl.

Suitable groups which confer solubility in water are the phosphonic acid group, the benzenedisulphonimide group and, above all, the sulphonic acid group.

Suitable oximinohydrazones are those of the formula

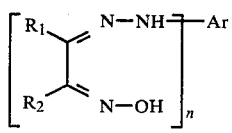

(II)

It is expedient to carry out the cyclodehydration of these compounds by stirring them in suitable vessels (for example low-pressure kettles) at pH values of 4–8.

The presence of buffer substances may be advantageous in order to establish this pH range.

In many cases, the presence of heavy metals or of salts thereof (in particular copper or copper-I and copper-II salts) has the effect of accelerating the reaction or increasing the yield. The end of the reaction can easily be determined analytically, for example by means of thin layer chromatography of a sample taken from the mixture. The 4,5-disubstituted v-triazolyl-acids or salts thereof which have been formed can be isolated, after cooling the reaction mixture, in a simple manner, for example by salting out.

The oximinohydrazones of the formula II used as starting materials do not need to be isolated for carrying out the process according to the invention. Rather, in a particularly advantageous embodiment of this process, the reaction mixture obtained in the condensation of the oximino-ketones of the formula

(III)

with the arylhydrazines

Ar—NH—NH$_2$ (IV)

is heated to the required reaction temperature without intermediate isolation, and if appropriate after distilling off any highly volatile solvent constituents present and after adding buffer salts and copper catalysts.

The preferred temperature range for this reaction is 140°–165° C.

Within this range, the reaction to give the triazole has in most cases ended after 5–6 hours.

EXAMPLE 1

3-(4-Ethyl-5-methyl-v-triazol-2-yl)-benzenesulphonic acid (Na salt).

1.5 l of water are initially introduced into a 3 l low-pressure kettle, and 570 g (3 mols) of phenylhydrazine-3-sulphonic acid and 360 g (3.1 mols) of oximinodiethyl ketone are added at room temperature, whilst stirring. The pH value is adjusted to 5.0–5.5 by dropwise addition of 40% strength sodium hydroxide solution, the mixture simultaneously being heated gradually to 55°. The phenylhydrazinesulphonic acid thereby disappears and the oximinohydrazone formed crystallises out. Under these conditions, the condensation reaction has ended after about 1–2 hours; the pH is then adjusted to 7 with sodium hydroxide solution (total consumption: about 200 ml of 40% strength sodium hydroxide solution; volume: about 2 l). 5 g of copper-I chloride are then added, the kettle is closed, and heated to 150° in the course of one hour, and the mixture is stirred at this temperature for a further 5–6 hours. Finally, the mixture is allowed to cool to 95°–98° and, after 15 g of active charcoal have been stirred in, the mixture is clarified through a suction filter; the pH value of the filtrate remains virtually unchanged (pH 7). The solution is concentrated to about 1.5 l. 80 g of sodium chloride are stirred in and the mixture is cooled gradually to 0°–5°. The sodium salt of 3-(4-ethyl-5-methyl-v-triazol-2-yl)- benzenesulphonic acid, which has precipitated as a thick crystal sludge, is filtered off, pressed out and dried at 110°. Yield: 782 g of 95% pure Na salt (86% of theory) in the form of colourless crystals.

The triazoles listed in the following table can be prepared in analogous yields and in an analogous manner.

TABLE

Triazoles of the formula

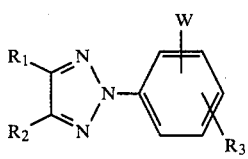

| Example | R₁ | R₂ | R₃ | W |
|---|---|---|---|---|
| 2 | C₂H₅ | CH₃ | H | 3-SO₃Na |
| 3 | C₂H₅ | CH₃ | H | 4-SO₃Na |
| 4 | C₆H₅– | CH₃ | H | 3-SO₃Na |
| 5 | C₆H₅– | CH₃ | H | 2-SO₃Na |
| 6 | C₆H₅– | C₂H₅ | H | 3-SO₃Na |
| 7 | C₆H₅– | CH₃ | 4-CH₃ | 3-SO₃Na |
| 8 | C₆H₅–C₆H₄– | | H | 3-SO₃Na |
| 9 | C₆H₅–C₆H₄– | CH₃ | H | 3-SO₃Na |
| 10 | Cl–C₆H₄– | CH₃ | H | 3-SO₃Na |
| 11 | CH₃–C₆H₄– | CH₃ | H | 3-SO₃Na |
| 12 | C₆H₅– | CH₃ | H | 4-PO₃Na₂ |
| 13 | C₂H₅ | CH₃ | H | 3-SO₂–NNa–SO₂–C₆H₅ |
| 14 | C₆H₅– | CH₃ | 4-Cl | 3-SO₃Na |

TABLE-continued

Triazoles of the formula

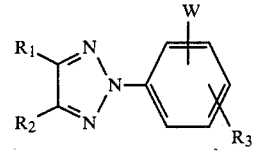

| Example | R₁ | R₂ | R₃ | W |
|---|---|---|---|---|
| 15 | C₃H₇ | C₂H₅ | H | 3-SO₃Na |
| 16 | CH₃ | CH₃ | H | 3-SO₃Na |

EXAMPLE 17

4,4'-Bis-(4-phenyl-5-methyl-v-triazol-2-yl)-stilbene-2,2'-disulphonic acid (Na salt).

80 g of 4,4'-dihydrazinostilbene-2,2'-disulphonic acid are suspended in 300 ml of water, and a solution of 70 g of oximinopropiophenone in 300 ml of methanol is added. The mixture is warmed gradually to 65° and the pH value is kept at 4.8-5.0 by stirring in sodium acetate (about 50 g). After about 3½ hours, the condensation reaction has ended; most of the methanol is then distilled off and 500 ml of cold water and 100 ml of concentrated sodium chloride solution are added. The condensation product which has precipitated is filtered off and suspended in 1.3 l of water, the suspension is adjusted to pH 7.5 with sodium acetate, and 2 g of copper-I chloride are added. The mixture is then heated to 155°, whilst stirring, and this temperature is maintained for a further 5 hours. Thereafter, the mixture is allowed to cool to 80°, 60 ml of concentrated sodium chloride solution are added and the bis-triazolylstilbene-disulphonic acid salt which has formed is filtered off, purified by recrystallising from aqueous methylglycol and dried. 99 g (71% of theory) of product are obtained in the form of yellow crystals.

I claim:

1. In the cyclodehydration of an α-oximinohydrazone of the formula

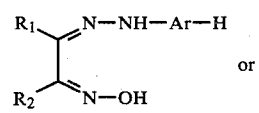

or

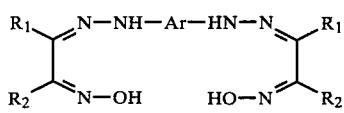

in which
R₁ and R₂ each independently is an optionally substituted alkyl or aryl radical, and
Ar is an arylene radical,
to produce the corresponding 2-aryl-v-triazole, the improvement which consists essentially of effecting the cyclodehydration at 120° to 200° C. in a predominantly aqueous medium.

2. The process according to claim 1, wherein the cyclodehydration is effected at 140° to 165° C.

* * * * *